(12) United States Patent
Scialdone

(10) Patent No.: US 10,071,127 B2
(45) Date of Patent: *Sep. 11, 2018

(54) HYDROGENATION OF CANNABIS OIL

(71) Applicant: Mark Andrew Scialdone, West Grove, PA (US)

(72) Inventor: Mark Andrew Scialdone, West Grove, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,633

(22) Filed: Jun. 5, 2017

(65) Prior Publication Data

US 2017/0266245 A1    Sep. 21, 2017

Related U.S. Application Data

(62) Division of application No. 15/149,721, filed on May 9, 2016, now Pat. No. 9,694,040.

(60) Provisional application No. 62/158,025, filed on May 7, 2015.

(51) Int. Cl.
| | |
|---|---|
| *A61K 36/00* | (2006.01) |
| *A61K 36/185* | (2006.01) |
| *A61K 31/352* | (2006.01) |
| *A61K 31/192* | (2006.01) |
| *A61K 31/05* | (2006.01) |

(52) U.S. Cl.
CPC .......... *A61K 36/185* (2013.01); *A61K 31/05* (2013.01); *A61K 31/192* (2013.01); *A61K 31/352* (2013.01); *A61K 2236/31* (2013.01)

(58) Field of Classification Search
CPC ..................................................... A61K 36/00
USPC ........................................................ 424/725
See application file for complete search history.

(56) References Cited

U.S. PATENT DOCUMENTS

| | | | |
|---|---|---|---|
| 2,419,937 A | 5/1947 | Adams | |
| 2015/0038567 A1 | 2/2015 | Herkenroth et al. | |

FOREIGN PATENT DOCUMENTS

| | | |
|---|---|---|
| WO | 2008113492 A1 | 9/2008 |
| WO | 2012144892 A1 | 10/2012 |

OTHER PUBLICATIONS

International Searching Authority, International Search Report and the Written Opinion for International Application No. PCT/US16/31441, dated Aug. 15, 2016.
Gaoni et al., "Hashish-VII the Isomerization of Cannabidiol to Tetrahydrocannabinols", Tetrahedron (1966), pp. 1481-1488, vol. 22.
Mechoulam et al., "Cannabidiol: an overview of some chemical and pharmacological aspects. Part I: chemical aspects", Chemistry and Physics of Lipids, Dec. 2002, pp. 35-43, vol. 121.
Dinesh Thapa et al., "Novel hexahydrocannabinol analogs as potential anti-cancer agents inhibit cell proliferation and tumor angiogenesis", European Journal of Pharmacology, Elsevier Science, NL, vol. 650, No. 1, Jan. 10, 2011, pp. 64-71.
Francoise Boucher et al., "Mise en evidence de deux types chemiques chez le Cannabis sativa originaire d'Afrique du sud", Phytochemistry, vol. 16, No. 9, Jan. 1, 1977, pp. 1445-1448.
Extended European Search Report, 16790224.6-1110/3291807 PCT/US2016031441, 8 pages.

*Primary Examiner* — Michael V Meller
(74) *Attorney, Agent, or Firm* — Eckert Seamans Cherin & Mellott, LLC; Carol A. Marmo

(57) ABSTRACT

The present invention relates to the extraction and hydrogenation of essential oil of a *cannabis* plant. The invention includes hydrogenated *cannabis* compounds and compositions, as well as methods of preparation and therapeutic uses for regressing tumors in a cancer patient. The extract can include 9-tetrahydrocannabinoic acid and 9-cannabidiolic acid, and the hydrogenated *cannabis* oil can include hydrogenated 9-tetrahydrocannabinoic acid, hydrogenated 9-cannabidioc acid and, mixtures and blends thereof.

3 Claims, 1 Drawing Sheet

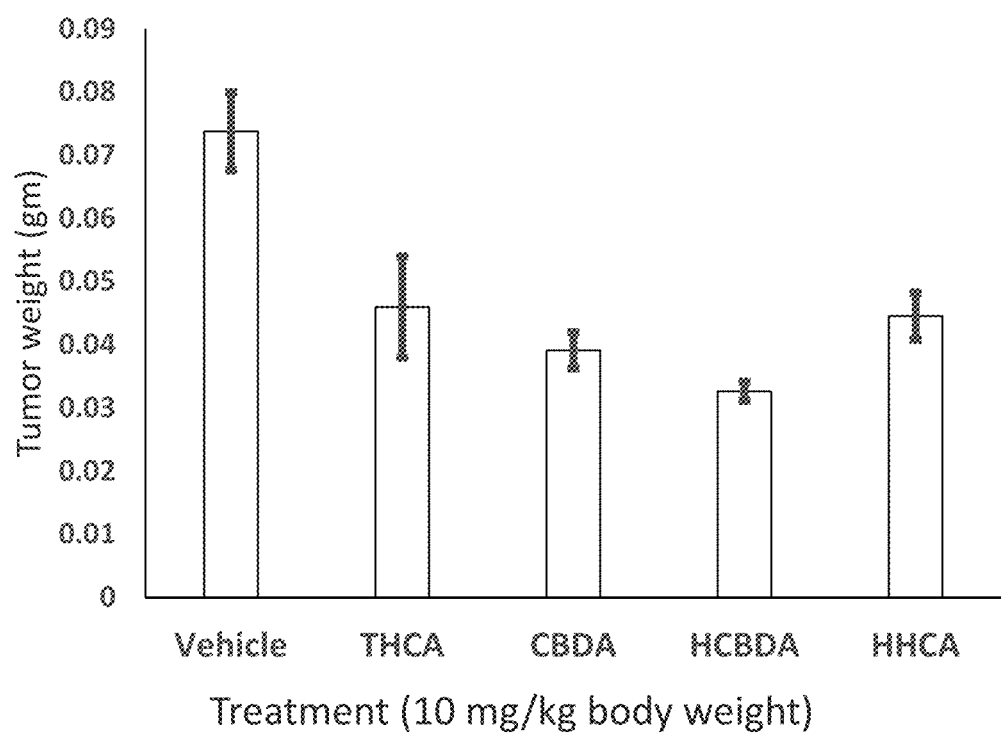

HYDROGENATION OF CANNABIS OIL

SUMMARY

The present invention relates to a product, e.g., compound, obtained from the hydrogenation of *cannabis* oil, compositions that include the product, and methods of preparing the product. Hydrogenation converts cannabinoids, as well as, terpenoids, flavonoids and sterols present in *cannabis* oil into their hydrogenated derivatives in a hydrogenated *cannabis* oil (HCO) mixture. The amounts of the hydrogenated compounds in the HCO product depends on the amounts of the precursors in the starting *cannabis* oil, which may vary based on the plant variety employed. Further, the hydrogenated compounds formed may depend on the hydrogenation reaction conditions used and different product compounds can be formed by changing the reaction conditions and hydrogenation catalyst used.

In one aspect, the present invention provides a method of hydrogenating *cannabis* oil that includes obtaining a *cannabis* plant having essential oil, including at least one of 9-tetrahydrocannabinoic acid and 9-cannabidiolic acid; extracting the essential oil from the *cannabis* plant to form an essential oil extract; and hydrogenating the essential oil extract to form hydrogenated *cannabis* oil, including at least one of hydrogenated 9-tetrahydrocannabinoic acid and 9-cannabidioc acid.

The extracting and hydrogenating steps can include extracting the essential oil from the *cannabis* plant employing an extraction solvent, separating an essential oil extract, including at least one of 9-tetrahydrocannabinoic acid and 9-cannabidiolic acid, and hydrogenating the essential oil extract in absence of the extraction solvent.

In another aspect, the present invention provides a hydrogenated *cannabis* oil composition that includes a hydrogentated acid selected from the group consisting of hydrogenated 9-tetrahydrocannabinoic acid, hydrogenated 9-cannabidioc acid and, mixtures and blends thereof.

In still another aspect, the present invention provides a method for regressing tumors in a cancer patient, including preparing hydrogenated *cannabis* oil composition, which includes obtaining a *cannabis* plant having essential oil, including at least one of 9-tetrahydrocannabinoic acid and 9-cannabidiolic acid, extracting the essential oil from the *cannabis* plant to form an essential oil extract, and hydrogenating the essential oil extract to form hydrogenated *cannabis* oil, including at least one of hydrogenated 9-tetrahydrocannabinoic acid and 9-cannabidioc acid; and administering a therapeutically effective amount of the hydrogenated *cannabis* oil composition to the cancer patient.

BRIEF DESCRIPTION OF THE DRAWING

FIG. 1 is a bar graph showing the effect of cannabinoids on the glioblastoma tumor (U87) weight following treatment of one week, in accordance with certain embodiments of the invention.

DETAILED DESCRIPTION OF THE PREFERRED EMBODIMENTS

The present invention relates to novel compounds, compositions and methods for extracting and hydrogenating essential oils of the *cannabis* plant. Hexahydrocannabanoids (HHCs) can be produced by hydrogenating mixtures of tetrahydrocannabanoid compounds, the principal component of the essential oil from *cannabis* plants, herein referred to as *cannabis* oil. *Cannabis* oil can be obtained from plants of the *Cannabis sativa*, *C. indica* and *C. ruderalis* by various conventional isolation processes, including steam distillation, organic solvent extraction, microwave-assisted organic solvent extraction, supercritical fluid extraction and cryomechanical methods. The crude *cannabis* oil, extract or concentrate obtained from these processes can be used without any purification to produce HHC-enriched *cannabis* oil by hydrogenation of the oil directly to reduce the carbon-carbon double bonds of the tetrahydrocannabinoid compounds in the oil such as Δ-9-tetrahydrocannabinoic acid (THCA) and Δ-9-cannabidioc acid (CBDA).

The direct hydrogenation of the crude *cannabis* oil will also hydrogenate the unsaturated groups in the other compounds present in *cannabis* oil such as terpenes, terpenoids, flavonoids, sterols and other unsaturated compounds. Chemical transformation of these compounds in *cannabis* oil by hydrogenation of their unsaturated functional groups changes the properties of the product herein referred to as hydrogenated *cannabis* oil (HCO). HCO is the product of *cannabis* oil hydrogenation that is enriched with hexahydrocannabanoids and hydrogenated terpenoids. The concentration of the individual cannabinoids and terpenes, which varies in different varieties of *cannabis* plants, in the starting *cannabis* oil determines the concentration of the hydrogenated compounds in the HCO product.

Thus, *cannabis* oil produced by extraction of whole plants can be used in the hydrogenation reaction to produce hydrogenated *cannabis* oil (HCO), which is enriched with HHCs, as well as hydrogenated terpenes, e.g., terpenoids.

As used herein, the following terms have the definitions provided.

The term "tetrahydrocannabinoic acids" as used herein refers to the compounds having the chemical structures of Δ-9-tetrahydrocannabinoic acid (THCA) and Δ-9-cannabidiolic acid (CBDA) as depicted in Formulas 1a and 1b.

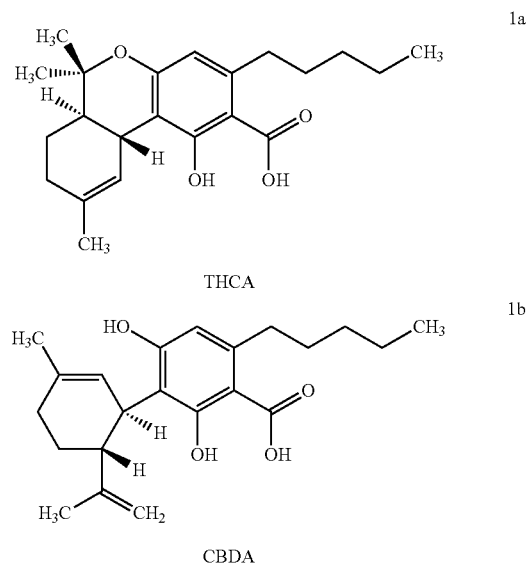

THCA

CBDA

The term "tetrahydrocannabinols" as used herein refers to the compounds having the chemical structures of THC and CBD as depicted in Formulas 2a and 2b.

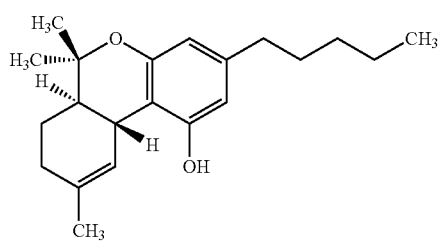

THC

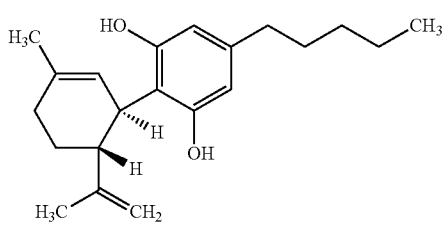

CBD

The term "hexahydrocannabanoids" ("HHC") formed by hydrogenation of cannabinoids as used herein refers to the compounds having the chemical structures of HTHCA, HCBDA, HTHC and HCBD as depicted in Formulas 3a, 3b, 3c and 3d.

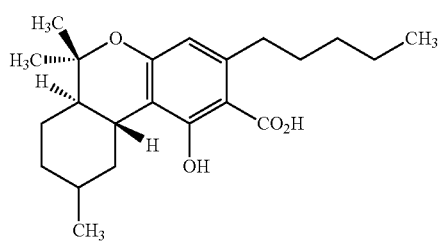

HTHCA

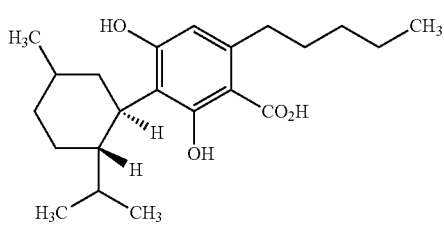

HCBDA

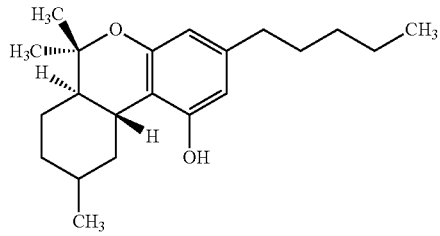

HTHC

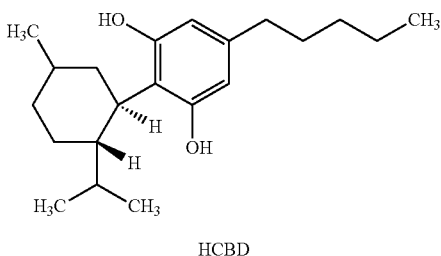

HCBD

The term "2-hydroxymethyl-hexahydrocannabanoids" ("2-HM-HHC") formed by hydrogenation of cannabinoids as used herein refers to the compounds having the chemical structures of 2-HMHTHC and 2-HMHCBT as depicted in Formulas 4a and 4b.

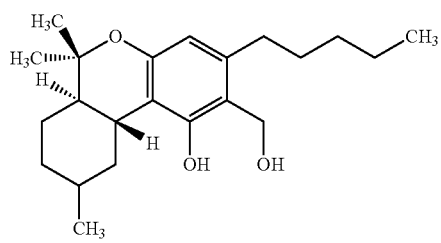

2-HMHTHC

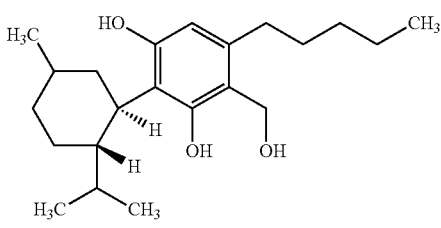

2-HMHCBT

The term "partially hydrogenated cannabidiol" ("PH-CBD") formed by hydrogenation of CBD to selectively reduce the isopropenyl group as used herein refers to the compound having the chemical structure as depicted in Formula 5.

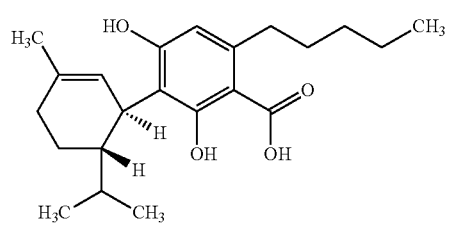

PHCBDA

The term "cannabis oil" as used herein refers to the isolated extract from cannabis plants. Cannabis oil is obtained from plants of the Cannabis sativa, C. indica and C. ruderalis by various isolation processes, including steam distillation, organic solvent extraction, microwave-assisted organic solvent extraction, supercritical fluid extraction and cryo-mechanical methods, which are suitable for use in this invention. Crude *cannabis* oil, extract or concentrate so obtained can be used without any purification to produce HHC-enriched *cannabis* oil by hydrogenation of the oil directly to reduce the carbon-carbon double bonds of the tetrahydrocannabinoid compounds in the oil such as Δ-9-tetrahydrocannabinoic acid (THCA) and Δ-9-cannabidiolic acid (CBDA).

The endocannabinoid system (ECS) is a chemical-based signaling system found throughout the human body in the brain, organs, connective tissues, glands, and immune cells. The ECS system functions based on ligands binding membrane bound G-protein coupled receptors, namely the CB1 and CB2 receptors. The known endocannahanoids are anandamide and 2-arachidonoylglycerol. The phytocannabinoids produced by *cannabis* also bind and activate these receptors.

Synthetic derivatives that are not plant-derived that have receptor subtype selectivity towards either CB1 or CB2 are known in the art.

The term "hydrogenation" as used herein refers to the chemical reaction of molecular hydrogen ($H_2$) with organic compounds resulting in the addition of a hydrogen molecule to the organic compound. The hydrogenation of organic compounds and mixtures of organic compounds is well known in the art. The hydrogenation of organic compounds and mixtures of organic compounds having carbon-carbon and carbon-oxygen double bonds is generally known in the art.

Catalytic hydrogenations employ catalysts that increase the rate of the reaction between the organic compounds. Hydrogenation catalysts used can be heterogeneous in the reaction medium, such as, a solution over a solid catalyst or homogeneous in the reaction solvent. The use of both heterogeneous and homogeneous catalysts in the hydrogenation of organic compounds and mixtures of organic compounds is also generally known in the art.

The term "catalyst" as used herein refers to a substance that affects the rate of a chemical reaction (but not the reaction equilibrium), and emerges from the process chemically unchanged. The term "promoter" as used herein refers to a compound that is added to enhance the physical or chemical function of a catalyst. A chemical promoter generally augments the activity of a catalyst, and may be incorporated into the catalyst during any step in the chemical processing of the catalyst constituent. The chemical promoter generally enhances the physical or chemical function of the catalyst agent, but can also be added to retard undesirable side reactions. A "metal promoter" refers to a metallic compound that is added to enhance the physical or chemical function of a catalyst.

Many hydrogenation catalysts are effective, including (without limitation) those containing as the principal component, e.g., element, iridium, palladium, rhodium, nickel, ruthenium, platinum, rhenium, compounds thereof, combinations thereof, and the supported versions thereof. A supported catalyst is one in which the active catalyst agent is deposited on a support material by spraying, soaking or physical mixing, followed by drying, calcination, and if necessary, activation through methods such as reduction or oxidation. Materials frequently used as support are porous solids with high total surface areas (external and internal) which can provide high concentrations of active sites per unit weight of catalyst. The catalyst support may enhance the function of the catalyst agent; and supported catalysts are generally preferred because the active metal catalyst is used more efficiently. A catalyst which is not supported on a catalyst support material is an unsupported catalyst. The metal catalyst used in the process of this invention may be used as a supported or as an unsupported catalyst.

The catalyst support can be any solid, inert substance including, but not limited to, oxides such as silica, alumina, titania, calcium carbonate, barium sulfate, and carbons. The catalyst support can be in the form of powder, granules, pellets, or the like. In certain embodiments, the support material of the present invention is selected from the group consisting of carbon, alumina, silica, silica-alumina, titania, titania-alumina, titania-silica, barium, calcium, compounds thereof and combinations thereof. Suitable supports include carbon, $SiO_2$, $CaCO_3$, $BaSO_4$ and $Al_2O_3$. Moreover, supported catalytic metals may have the same supporting material or different supporting materials. In one embodiment of the instant invention, the support is carbon. Further, the supports, e.g., carbon, can have a surface area from about 100 to about 200 $m^2/g$. Furthermore, the supports, e.g., carbon, can have a surface area of at least about 200 $m^2/g$ or at least about 300 $m^2/g$.

Commercially available carbons which may be used in this invention as catalyst supports include those sold under the following trademarks: Bameby & SutclilTe™, Darco™, Nuchar™, Columbia JXN™, Columbia LCK™, Calgon PCB™, Calgon BPL™, Westvaco™, Norit™ and Barnaby Cheny NB™. The commercially available carbon can also include Calsicat C, Sibunit C, or Calgon C (commercially available under the registered trademark Centaur®). In certain embodiments, combinations of catalytic metal and support system include nickel on carbon, nickel on $Al_2O_3$, nickel on $CaCO_3$, nickel on $BaSO_4$, nickel on $SiO_2$, platinum on carbon, platinum on $Al_2O_3$, platinum on $CaCO_3$, platinum on $BaSO_4$, platinum on $SiO_2$, palladium on carbon, palladium on $Al_2O_3$, palladium on $CaCO_3$, palladium on $BaSO_4$, palladium on $SiO_2$, iridium on carbon, iridium on $Al_2O_3$, iridium on $SiO_2$, iridium on $CaCO_3$, iridium on $BaSO_4$, rhenium on carbon, rhenium on $Al_2O_3$, rhenium on $SiO_2$, rhenium on $CaCO_3$, rhenium on $BaSO_4$, rhodium on carbon, rhodium on $Al_2O_3$, rhodium on $SiO_2$, rhodium on $CaCO_3$, rhodium on $BaSO_4$, ruthenium on carbon, ruthenium on $Al_2O_3$, ruthenium on $CaCO_3$, ruthenium on $BaSO_4$, and ruthenium on $SiO_2$. As stated above, useful catalytic metals include component, e.g., elemental, iridium, palladium, rhodium, nickel, ruthenium, platinum and rhenium; and useful support materials include carbon, alumina, silica, silica-alumina, titania, titania-alumina, titania-silica, barium and calcium, and more particularly, carbon, $SiO_2$, $CaCO_3$, $BaSO_4$ and $Al_2O_3$.

A supported catalyst may be made from any combination of the above named metals and support materials. A supported catalyst may also, however, be made from combinations of various metals and/or various support materials selected from subgroup(s) of the foregoing formed by omitting any one or more members from the whole groups as set forth in the lists above. As a result, the supported catalyst may, in such instance, not only be made from one or more metals and/or support materials selected from subgroup(s) of any size that may be formed from the whole groups as set forth in the lists above, but may also be made in the absence of the members that have been omitted from the whole groups to form the subgroup(s). The subgroup(s) formed by omitting various members from the whole groups in the lists above may, moreover, contain any number of the members of the whole groups such that those members of the whole groups that are excluded to form the subgroup(s) are absent from the subgroup(s). For example, it may be desired in certain instances to run the process in the absence of a catalyst formed from palladium on carbon.

While the weight percent of catalyst on the support is not critical, it will be appreciated that the higher the weight percent of metal, the faster the reaction. In certain embodiments, the content range of the metal in a supported catalyst is from about 0.1 wt % to about 20 wt % of the whole of the supported catalyst (catalyst weight plus the support weight). In other embodiments, the catalytic metal content range is from about 1 wt % to about 10 wt % by weight of the whole of the supported catalyst. Still further, another catalytic metal content range is from about 3 wt % to about 7 wt % by weight of the whole of the supported catalyst. Optionally, a metal promoter may be used with the catalytic metal in the method of the present invention. Suitable metal promoters include: 1) those elements from Groups 1 and 2 of the Periodic Table; 2) tin, copper, gold, silver, and combinations thereof; and 3) combinations of Group 8 metals of the Periodic Table in lesser amounts.

Temperature, solvent, catalyst, pressure and mixing rate are all parameters that affect the hydrogenation. The relationships among these parameters may be adjusted to effect the desired conversion, reaction rate, and selectivity in the reaction of the process. Within the context of the present invention, in certain embodiments, the temperature is from about 25° C. to 250° C., or from about 50° C. to about 150° C., or from about 50° C. to 100° C.

In certain embodiments, the hydrogen pressure is from about 0.1 to about 20 MPa, or from about 0.3 to 10 MPa, or from about 0.3 to 4 MPa.

The reaction may be performed neat or in the presence of a solvent. Useful solvents include those known in the art for use in hydrogenation reactions, such as, hydrocarbons, ethers, alcohols and mixtures and blends thereof. In certain embodiments, alcohols are used, e.g., lower alkanols, such as, methanol, ethanol, propanol, butanol, and pentanol.

Where the reaction is carried out according to certain embodiments, selectivity in the range of at least 70% is attainable where selectivity of at least 85% may be typical. Selectivity is the weight percent of the converted material that is HCO where the converted material is the portion of the starting material that participates in the hydrogenation reaction.

The process of the present invention may be carried out in batch, sequential batch (i.e. a series of batch reactors) or in continuous mode in any of the equipment customarily employed for continuous processes.

In U.S. Pat. No. 2,419,937, the hydrogenation of THC as a pure compound to HHC using a heterogeneous catalyst ($Pt_2O$, Adams catalyst) is disclosed. The purified THC used was synthesized by the acid catalyzed isomerization of CDB that was isolated from "red oil" hemp extract by precipitation in a procedure described in U.S. Pat. No. 2,304,669.

A method for the selective hydrogenation of the isopropenyl moiety of the terpene L-carvone using the homogeneous catalyst tris-triphenylphosphine rhodium chloride (Wilkinson's catalyst) is known in the art.

While hydrogenation of isolated, pure CBD and THC to their corresponding hexahydro derivatives is known, e.g., as reported in Tetrahedron 1966, Vol. 22, pp. 1481 to 1488, the direct hydrogenation of *cannabis* oil or extract comprising mixtures of CBDA, THCA and other cannabinoids, terpenoids and flavonoids, sterols and other minor compounds present in the oil or extract, is novel. Hydrogenation converts the unsaturated groups, here defined as non-aromatic carbon-carbon double bonds in the cannabinoids, terpenoids, flavonoids, sterols and other minor compounds present in the oil or extract into saturated groups by the addition of hydrogen to the molecules. This hydrogenation or saturation of the unsaturated groups changes the properties of the hydrogenated product oil, such as, improvements in color, essence, taste, smell, stability and biological activity.

*Cannabis* oil also includes unsaturated compounds such as the monoterpenoids carvone, limonene, myrcene, linalool, pulegone, 1,8-cineole, α-pinene, α-terpineol, terpineol-4-ol, p-cymene, borneol, Δ-3-carene, geraniol, citronellal, citronellol, citral, cyclocitral and the sesquiterpenes β-caryophyllene and nerolidols. The carbon-carbon double bonds in the molecules react with hydrogen in the hydrogenation of *cannabis* oil.

In addition, there are sterols and flavonoid compounds in *cannabis* oil that contain carbon-carbon double bonds that will react with hydrogen in the hydrogenation of *cannabis* oil.

Different reactions conditions (catalyst, solvent, temperature, pressure) in the hydrogenation of *cannabis* oil determine the compounds formed in the reaction and thus the molecular makeup of the HCO product.

*Cannabis* oil can be obtained from the *cannabis* plant using various conventional extraction techniques and apparatus that is known in the art. For example, *cannabis* oil is obtained from plants of the *Cannabis sativa*, *C. indica* and *C. ruderalis* by various isolation processes, including steam distillation, organic solvent extraction, microwave-assisted organic solvent extraction, supercritical fluid extraction and cryo-mechanical methods are suitable for use in this invention. A *cannabis* extract including crude *cannabis* oil, in the presence of absence of a solvent, is suitable for use in this invention directly without isolation of the *cannabis* oil, extract or concentrate. A *cannabis* extract so obtained can be used without any purification. In certain embodiments, direct hydrogenation of *cannabis* extract is performed.

A *cannabis* extract including crude *cannabis* oil and a volatile solvent can be purified by de-fatting the extract by a cooling process known as winterization, which precipitates the lipid fraction from the extract. A purified, de-fatted *cannabis* extract so obtained is suitable for use in this invention. Direct hydrogenation of de-fatted *cannabis* extract is preferred.

The hydrogenation reaction may be carried out in batch in a single reactor, in sequential batch in a series of reactors, in reaction zones within one or more reactors, or in continuous mode in any of the equipment customarily employed for continuous processes.

In certain embodiments, the extraction and hydrogenation process can be conducted as follows. A *cannabis* plant is harvested. It is known that decarboxylation of the essential oil is initiated upon harvesting and subsequent aging of the *cannabis* plant. At room temperature, decarboxylation is minimal. However, increased temperature, e.g., by heating, accelerates the decarboxylation process. With minimal decarboxylation, the *cannabis* plant and essential oil contained therein are enriched with THCA and/or CBDA as shown in Formulas 1a and 1b, respectively. The essential oil is extracted using a conventional extraction process, such as, solvent extraction, in the absence of heating or at a low temperature, to produce a *cannabis* oil extraction enriched in THCA and/or CBDA. In order to retain a significant concentration or level of THCA and CBDA, e.g., acids, in the essential oil and the extract resulting therefrom, the *cannabis* plant may be frozen after being harvested. Thus, extraction of the essential oil of the *cannabis* plant can produce THCA-enriched extract or CBDA-enriched extract or THCA- and CBDA-enriched extract. The essential oil extract is hydrogenated using conventional hydrogenation techniques and apparatus known in the art. As previously described, hydrogenation generally refers to treating a compound or composition with hydrogen, e.g., a chemical reaction between molecular hydrogen (e.g., $H_2$) typically in the presence of a catalyst, such as, but not limited to, nickel, palladium or platinum. Hydrogenation results in reducing double bond(s) in a compound, e.g., hydrocarbon. Upon removal of any solvent, hydrogenated essential oil enriched in HTHCA and/or HCBDA, as shown in Formulas 3a and 3b, respectively, is produced.

In certain embodiments, the hydrogenation is conducted on an isolated *cannabis* extract, e.g., a *cannabis* extract that has been separated from, and is free of, extraction solvent. In other embodiments, the hydrogenation is conducted on a *cannabis* extract that includes the presence of an extraction solvent, such as, saturated hydrocarbon, including but not limited to, butane, propane and mixtures and blends thereof.

Following the hydrogenation reaction, the hydrogenated *cannabis* oil can be recovered from the reaction mixture by methods of separation well-known to those skilled in the art, such as decantation or filtration. HHCs can be isolated and purified from the hydrogenated *cannabis* oil, for example, by column chromatography.

In addition to the THCA and/or CBDA being hydrogenated to HTHCA and/or HCBDA, respectively, other components of the essential oil of the *cannabis* plant can be hydrogenated. For example, it is contemplated that the THCA- and/or CBDA-enriched oil and extract will also contain THC and CBD, as shown in Formulas 2a and 2b, respectively, since some level or degree of decarboxylation occurs as a result of harvesting, and any subsequent aging of, the *cannabis* plant. Although, the concentration or level of THCA and/or CBDA in the essential oil and extract will be greater than the concentration or level of THC and/or CBD. Thus, the HCO can also include HTHC and/or HCBD, as shown in Formulas 3c and 3d, respectively (e.g., in a lesser amount than the THCA and/or CBDA). Furthermore, as aforementioned, terpenoids flavonoids, sterols and other minor compounds that are present in the oil and extract are also hydrogenated in the process of hydrogenating the essential oil and therefore, be present (e.g., in a lesser amount than the THCA and/or CBDA) in the HCO.

Cannabinoid and cannabinoid derivatives are useful in the treatment of many diseases some of which are mediated by the endocannabinoid system are well known in the art. Cannabinoid receptor subtypes CB1 and CB2 as well as both synthetic antagonists and agonists that modulate those receptors are also well known in the art. Therapeutic applications can be administered to treat various conditions and diseases, such as, cancer, epilepsy, post-traumatic stress disorder, diabetes, Crohn's disease, gout, pain relief, glaucoma, opioid dependence, alcohol abuse, insomnia, psoriasis, shingles, anorexia, asthma, fibromyalgia, rheumatoid arthritis, migraine headaches, Dravet syndrome, multiple sclerosis, autism, and menstrual pain.

Excessive abdominal obesity along with other risk factors results in the metabolic syndrome, which can lead to heart disease, Type-2 diabetes, and death. The endocannabinoid system (ECS) is composed of neutral lipids which signal through the G-protein coupled cannabinoid receptors CB1 and CB2. In abdominal obesity, the ECS is generally up-regulated in central and peripheral tissues and its blockade results in positive metabolic changes.

The CB1 receptor is implicated in the maintenance of homeostasis and is potentially a clinically relevant target for the design of therapies against metabolic syndrome, deserving the development and clinical testing of CB1-neutral antagonists which can pass the blood-brain barrier or of peripherally restricted inverse agonists/neutral antagonists. Selective CB1 antagonists are useful in weight reduction and smoking cessation.

Selective CB1 agonists may be used to isolate the effects of receptor from the CB2 receptor as most cannabinoids and endocannabinoids bind to both receptor subtypes.

As can be demonstrated by competitive binding assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as pharmaceutical compositions, e.g., drugs, for the treatment of the following disease-states, conditions or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis *nodosa*, polyarteritis *nodosa*, periarteritis *nodosa*, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; and pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; and extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; Graves disease; and type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, post-operative pain, traumatic pain, muscle pain, pain in burned skin, sun burn, trigeminal neuralgia, sun burn; spasm of the gastrointestinal tract or uterus, and colic;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, and myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post-surgical pain, stump pain, repetitive motion pain, pain induced by post mastectomy syndrome, multiple sclerosis, root avulsions, postthoracotomy syndrome, neuropathic pain associated hyperalgesia and allodynia;

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus and erythematosus;

(xxii) Cancer pain induced by or associated with tumors such as lymphatic leukemia; Hodgkin's disease, malignant lymphoma; lymphogranulomatoses; lympho sarcoma; solid malignant tumors; extensive metastases;

(xxiii) Headache such as cluster headache, migraine with and without aura, tension type headache, headache with different origins, headache disorders including prophylactic and acute use; and (xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; in certain embodiments, from about 0.1 mg to about 20 mg/kg of body weight per dosage. For example, for administration to a 70 kg person, the dosage range would be from about 0.7 mg to about 7000 mg per dosage of a compound of the invention, or from about 7.0 mg to about 1400 mg per dosage. Some degree of routine dose optimization may be required to determine an optimal dosing level and pattern. The active ingredient may be administered from 1 to 6 times daily.

HCO can be administered by vaporization, smoking or making use of a carrier food, edible or pharmaceutical composition. When used as pharmaceuticals, the HCO is typically compositions can be prepared using procedures well known in the pharmaceutical art and comprise the HCO products of this invention. The HCO products may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the HCO products of this invention are administered in a therapeutically or pharmaceutically effective amount, but may be administered in lower amounts for diagnostic or other purposes.

Methods of administration of HCO in pure form or in an appropriate pharmaceutical composition can be carried out using any of the accepted modes of administration of pharmaceutical compositions, Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art.

Pharmaceutical compositions suitable for buccal (sublingual) administration include lozenges including a compound of the present invention in a flavored base, usually sucrose, and acacia or tragacanth, and pastilles including the compound in an inert base such as gelatin and glycerin or sucrose and acacia.

Pharmaceutical compositions suitable for parenteral administration include sterile aqueous preparations of a compound of the present invention. In certain embodiments, these preparations are administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water. Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a The HCO product of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, in certain embodiments, compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the HCO product is from about 1% to 35%, or from about 3% to 15%.

For administration by inhalation, the HCO products of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

EXAMPLES

The present invention is further defined in the following examples. These examples are given by way of illustration only. From the above discussion and these examples, the artisan can ascertain the essential characteristics of this invention, and, without departing from the spirit and scope thereof, can make various changes and modifications of the invention to adapt it to various usages and conditions.

The following abbreviations are used: GC is gas chromatography; GC-MS is gas chromatography-mass spectrometry; FID is flame ionization detector; NMR is nuclear magnetic resonance; ° C. is degrees Centigrade; MPa is mega Pascal; kPa is kilo Pascal; Pa is Pascal; rpm is revolutions per minute; mL is milliliter; CMO is *cannabis* oil; wt % is weight percent; TOS is time on stream; NPL is tetrahydrocannabanoids; HHC is hexahydrocannabanoids; h is hour; conc. is concentration; conv. is conversion; temp. is temperature; ° C. is degrees Centigrade; kg is kilogram; XRF is X-ray fluorescence spectroscopy; ppm is parts per million.

Example 1

Pre-extracted *cannabis* extract (374 mg) enriched with THCA was obtained. In a 100-mL round-bottomed flask, the *cannabis* extract in absolute ethanol (20 mL) was treated with 10% Pd/C (36 mg, Aldrich) and stirred under nitrogen at room temperature. Hydrogen gas was flushed in the vessel and bubbled through the mixture. The mixture was stirred under a balloon of hydrogen overnight. The mixture was filtered through a bed of Celite. Thin layer chromatography showed a slightly less polar spot (30% ethyl acetate/hexanes on silica gel plates). The solvent was removed by roto-evaporation to yield an HTHCA product as a clear oil (330 mg) characterized by NMR and MS. The $^{13}$C NMR spectrum of the product showed loss of the olefinic carbons at 124 and 132 ppm respectively. The molecular weight was confirmed by high resolution mass spectroscopy where the observed M+H was 361.2375.

Example 2

Pre-extracted *cannabis* extract (100 mg) enriched with CBDA was obtained. In a 50-mL round-bottomed flask, the *cannabis* extract in absolute ethanol (10 mL) was treated with 10% Pd/C (10 mg, Aldrich) and stirred under nitrogen at room temperature. Hydrogen gas was flushed in the vessel and bubbled through the mixture. The mixture was stirred under a balloon of hydrogen overnight. The mixture was filtered through a bed of Celite. Thin layer chromatography showed a slightly less polar spot (30% ethyl acetate/hexanes on silica gel plates). The solvent was removed by roto-evaporation to yield the HCBDA product as a pale oil (86 mg) characterized by NMR and MS. The NMR spectrum of the product showed loss of all olefinic carbons. The molecular weight was confirmed by mass spectroscopy where both the mono and dihydrogenated adducts were observed as ammonium salts at 377 and 375 (the starting material showed an ammonium salt at 373 m/e).

Example 3

The effect of the hydrogenated and non-hydrogenated *cannabis* oil on tumor growth and angiogenesis were evaluated by implanting U87 (Human glioblastoma) 3×106 cells (50% matrigel) in three female athymic mice. The site of implantation was subcutaneous with two implants per mouse. The date of implantation was Feb. 1, 2016 and the date of administering treatment was Feb. 3, 2016. There were three mice in each of the following groups, and the treatment consisted of feeding each of the three mice 10 mg/kg body weight of the treatment corresponding to each one of the following groups:
1. Untreated Vehicle
2. THCA
3. CBDA
4. HCBDA
5. HTHCA The termination date was Feb. 11, 2016. On this date, the tumors were excised and weighed. The results are shown in Table 1 and illustrated in the below plot.

TABLE 1

| Treatment | Tumor weight (mg) |
| --- | --- |
| Vehicle | 73.8 |
| THCA | 46.0 |
| CBDA | 39.1 |
| HCBDA | 32.6 |
| HTHCA | 44.5 |

Table 1 shows that for the untreated "Vehicle" group, the average weight of the excised tumors for the three mice was 73.8 mg, i.e., total weight of the excised tumors/six tumors (i.e., two tumors in each of the three mice). It was assumed that the excised tumor weight for the "Untreated Vehicle" was essentially equivalent to its starting tumor weight. Thus, the results show that each of the THCA, CBDA, HCBDA and HTHCA treatments were effective to reduce tumor weight.

The invention claimed is:

1. An isolated hexahydrocannabinoid of formula 3a:

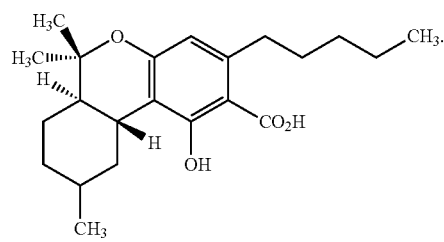

2. An isolated hexahydrocannabinoid of formula 4a:

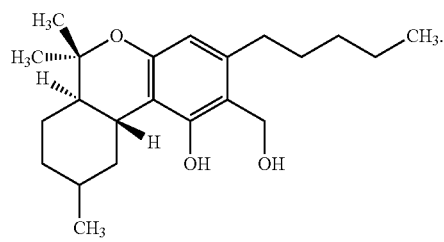

3. An isolated hexahydrocannabinoid of formula 4b:

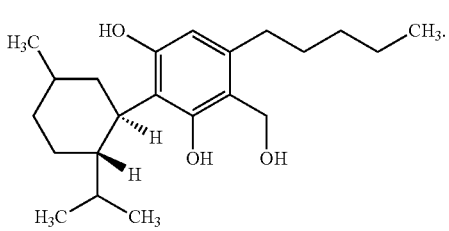

* * * * *